United States Patent [19]

Bakamjian

[11] 4,184,562
[45] Jan. 22, 1980

[54] MULTI-DIRECTIONAL ASSEMBLIES FOR SONIC LOGGING

[75] Inventor: Barkev Y. Bakamjian, Tulsa, Okla.

[73] Assignee: Standard Oil Company (Indiana), Chicago, Ill.

[21] Appl. No.: 851,088

[22] Filed: Nov. 14, 1977

[51] Int. Cl.² .............................................. G01V 1/40
[52] U.S. Cl. ..................... 181/104; 181/108; 73/622; 340/15.5 BH; 367/86; 367/180
[58] Field of Search .............. 181/102, 104, 105, 108, 181/155; 340/18 R, 8 FT, 15.5 BH; 73/622, 623

[56] References Cited

U.S. PATENT DOCUMENTS

| | | | |
|---|---|---|---|
| 3,028,752 | 4/1962 | Bacon | 340/8 FT |
| 3,136,381 | 6/1964 | Anderson | 340/15.5 BH |
| 3,481,425 | 12/1969 | Smith, Jr. et al. | 340/18 R |
| 3,504,759 | 4/1970 | Cubberly, Jr. | 181/104 |
| 3,542,150 | 11/1970 | Youmans et al. | 181/104 |
| 3,786,757 | 1/1974 | Goldstein et al. | 102/213 |
| 3,974,476 | 8/1976 | Cowles | 340/18 R |
| 3,978,939 | 9/1976 | Trouiller | 181/104 |
| 4,022,055 | 5/1977 | Flournoy et al. | 73/622 |

FOREIGN PATENT DOCUMENTS 143597  10/1948  Australia ................................. 181/155

Primary Examiner—Howard A. Birmiel
Attorney, Agent, or Firm—James H. Dautremont; Arthur McIlroy

[57] ABSTRACT

Electroacoustical transmitting or receiving transducer comprising a flat disc piezoelectric transducer element aligned with a conical reflector. The disc transducer element is positioned to transmit acoustic energy in a direction parallel with a borehole axis and this energy is reflected by the conical reflector so that it impinges upon a borehole wall near the critical angle to provide maximum propagation of energy in the rock in one direction parallel to the borehole. The same transducer arrangement also functions as an efficient directional receiver of acoustic energy.

14 Claims, 3 Drawing Figures

MULTI-DIRECTIONAL ASSEMBLIES FOR SONIC LOGGING

BACKGROUND OF THE INVENTION

This invention relates to sonic borehole logging tools and more particularly to a transducer assembly which directs acoustical energy at a preselected angle with respect to a borehole wall.

The following patents are believed to be relevant to the present invention: U.S. Pat. No. 3,974,476, issued to Cowles on Aug. 10, 1976; and U.S. Pat. No. 3,978,939, issued to Trouiller on Sept. 7, 1976.

The Trouiller patent provides a fairly complete statement of the prior art in the field of acoustic or velocity well logging. Such logging basically involves the injection of acoustic energy into a borehole wall at one point and the reception of part of that energy which has been transmitted back into the borehole at another point. The time lag between transmission and reception can be used to indicate acoustic energy velocity and other parameters. More accurate equipment has a single transmitting transducer and two receiving transducers with the time measurement being made between the reception at the two transducers which are spaced apart a known distance. The transducers which have typically been used are hollow cylindrical elements made of magnetostrictive or piezoelectric materials. Such elements are illustrated in FIG. 1 of the Trouiller patent. These elements transmit a majority of their acoustic energy straight out into the formation in a disc-shaped pattern perpendicular to the borehole axis. Such a pattern is illustrated in FIG. 4 of Trouiller. The energy which is thus transmitted straight out into the formation does not travel along the borehole wall where it can be received by receiving transducers. Thus, in the known devices only a small portion of the transmitted energy ever reaches the receiving transducer. As is known in the art and also illustrated by Trouiller in FIG. 5 of his patent, there is a critical angle of incidence at which acoustic energy impinging on the borehole wall will be refracted and travel through the borehole wall essentially parallel to the borehole. The ideal transducer would transmit 100% of its energy at or just below this critical angle so that essentially all of it would be traveling parallel to the borehole after incidence on the borehole wall. The Trouiller patent describes an improvement over prior art systems in which a solid cylindrical transducer element placed perpendicular to the borehole wall is used for both transmitting and receiving acoustical energy. As illustrated in FIG. 9 of Trouiller, such a cylindrical transducer is essentially omnidirectional, that is, transmits energy equally well in all directions perpendicular to its axis. Thus, Trouiller provides a transducer in which a significant amount of the transmitted energy does impinge upon the borehole wall at or near the critical angle. This is a significant improvement over the prior art cylindrical elements positioned parallel to the borehole wall in which only edge effect transmissions, which account for a very small part of the transmitted energy, actually impinge upon the borehole wall at the desired angle.

The Cowles patent illustrates a different type of borehole surveying tool. In this tool the energy is intentionally transmitted at right angles to the borehole wall, since reflection of energy from casing, borehole wall, fractures, etc., directly back into the same transducer is what is desired. The Cowles patent illustrates the use of an essentially flat disc-shaped transducing element and a flat reflecting element for directing energy into the borehole wall.

Thus, it is seen that in sonic logging tools of the type wherein acoustic energy is injected into a borehole wall to travel along the wall and is detected by one or more spaced receiving transducers, no transducers are available which direct substantially all of their acoustical energy at the borehole wall at or near the preferred critical angle.

Accordingly, an object of the present invention is to provide an acoustical energy transducer assembly for use in sonic logging in which substantially all of the transmitted acoustical energy is directed at a borehole wall at or near a critical angle.

Another object of the present invention is to provide an acoustic transducer assembly for borehole sonic logging which has essetially unidirectional response, that is, transmits or receives acoustical energy either up or down the borehole wall, but not both at the same time.

DESCRIPTION OF THE PREFERRED EMBODIMENT

Figure 1:
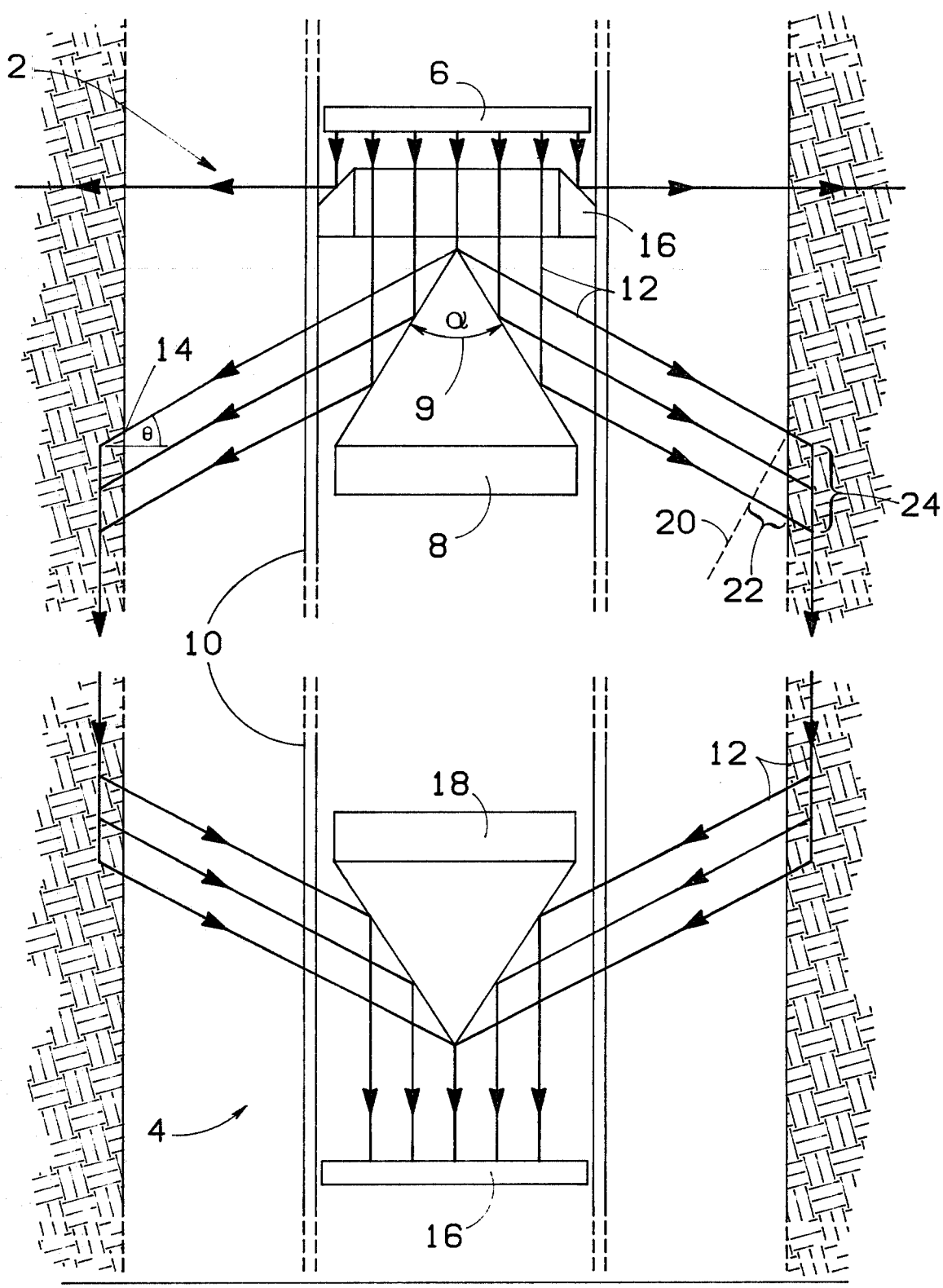
FIG. 1 is a cross-sectional illustration of transmitting and receiving transducer assemblies according to the present invention positioned in a borehole for sonic logging.

FIG. 1 illustrates a simple logging device having a transmitting transducer assembly shown generally at 2 and a receiving transducer assembly shown generally at 4. Transmitting transducer assembly 2 includes a flat disc transducer 6 positioned perpendicular to the borehole axis and a conical reflector 8 positioned with its axis in alignment with the borehole axis. These elements 6 and 8 are mounted within a cylindrical housing or sonde body 10 made of material such as rubber or Teflon which is essentially transparent at the acoustic frequencies involved in sonic logging. Transducer element 6 is in the preferred embodiment a piezoelectric device, but a magnetostrictive device could be substituted for transducer 6. The preferred embodiment was tested by construction of a small-scale laboratory sonic device in which a lead metaniobate crystal of approximately ⅜" diameter was used for transducer 6. While this transducer had a free resonant frequency of 1 megahertz, it was mounted with a sound-absorbing backing which resulted in providing a resonant frequency of approximately 250 to 300 KHz. Conical reflector 8 was machined out of a sound-reflecting material which in the preferred embodiment was aluminum but steel was also used successfully. The angle of the cone illustrated at 9 is selected to provide an angle of incidence at the borehole wall near the critical angle for the particular borehole wall material which is expected and the particular mode of propagation, shear or compressional, which is desired. Acoustic energy paths in this device are illustrated by the lines 12, with the arrowheads indicating direction of travel. The angle $\theta_c$ indicated at 14 is the angle of incidence which is selected by selecting the angle of cone 8.

While cone 8 is illustrated only in cross section, it is to be understood that it is completely symmetrical with respect to the borehole axis. Cone 8 has a circular cross section when viewed from above. In the laboratory model element 6 and cone 8 each had a hole which was concentric with the borehole axis. A rigid tube was inserted through the holes in elements 6 and 8 and in similar fashion through the receiving transducer assembly 4 to provide mechanical support and an electrical conduit to the receiver. In another version the elements were supported by three vertical rods spaced symmetrically on the circumferences of each element, such as 6 and 8.

Also illustrated in FIG. 1 is a collimator 16 intended for deflecting energy coming from the edges of transducer 6, which would tend to be nonparallel with the borehole axis. The illustrated collimator would be an aluminum ring with a 45-degree angle slope on its top side to reflect part of the energy directly out into the formation where it would not interfere to any great degree with the desired direction of propagation. Such a collimator has not actually been used in tests and experience to date indicates it is probably not necessary. In addition, the energy which would be sent directly into the formation by collimator 16 could possibly get into the actual signal path and interfere with proper operations. Therefore, it might be more appropriate to replace the illustrated collimator with a ring of acoustical absorptive material which would prevent this undesired energy from ever entering the borehole wall. As will be explained more fully below, the slight distortion caused by the edge effects may be in fact a desirable effect.

The receiving transducer 4 comprises an electroacoustical transducer element 16 and a reflecting cone 18, which are essentially identical to the transducer element 6 and cone 8, making up transducer assembly 2. The angles of cones 8 and 18 may be made slightly different to spread the angular response of a logging tool. As illustrated, receiver 4 would not use any type of collimator 16. It is apparent that more than one receiving transducer 4 may be employed for borehole logging and as stated above typically two such receivers spaced a known distance apart would be used. As illustrated by the acoustic raypaths 12, receiving assembly 4 efficiently receives acoustic energy refracted back into the borehole from the borehole wall, but only from one direction.

A borehole logging device, according to the present invention, is used in essentially the same manner as prior art sonic borehole logging devices. The device is positioned in a borehole in essentially the same manner as illustrated in the FIG. 1. The sonde is supported by a wireline cable extending from the sonde to lifting equipment at the surface. The cable contains sufficient electrical conductors to provide connections to the transducers 6 and 16 and any additional transducers which might be employed. A short electrical signal, ideally an impulse and more practically a short wavelet, is applied to the transmitting transducer 6. The transducer 6 transmits an essentially collimated beam of acoustical energy parallel to the borehole axis and toward the conical reflector 8. The angle of the conical reflector is selected so that when the acoustical energy is reflected off of its conical surface, it is traveling at an angle with respect to the borehole wall near the critical angle. Acoustical energy impinging upon the borehole wall at the critical angle passes into the rock and is refracted so that it moves through the rock in a direction essentially parallel to the borehole axis. As the energy passes down the borehole wall, measurable amounts of this energy pass back into the borehole itself and are diffracted again so that they are traveling at essentially the critical angle. The angle of the receiving cone 18 is again selected so that energy impinging upon it at the critical angle forms a collimated beam which is then reflected onto the surface of receiving transducer 16. The acoustical energy impinging on transducer 16 in turn generates an electrical signal which is then coupled by wires back to the surface for detection and recording.

As discussed in the above-referenced Trouiller patent, energy entering the formation from various portions of prior art transducers is out of phase and destructive interference results in loss of signal strength. In the present apparatus, such interference is essentially eliminated. The raypaths 12 from element 6 to a dotted line 20 are all of equal length and travel in the same medium. The various paths are therefore in phase at line 20. The lower ray travels the additional distance 22 in the borehole fluid before reaching the wall. The upper ray travels the additional distance 24 in the wall before reaching the point where the lower ray entered the wall. The ratio of velocities is such that the combined upper and lower rays are in phase when the raypaths are directed to the wall at the critical angle. This is more clear when it is considered in view of the fact that the critical angle is that angle whose sine equals the ratio of velocity in the wall to the velocity in the borehole fluid. This desirable phase characteristic also occurs with the receiver assembly 4.

In laboratory tests of this device it was expected that at angles beyond the critical angle no signal would be received in the receiving transducer. If this were absolutely true, then there would be a problem in selecting a cone angle for a given borehole, since in actual practice the critical angle varies with parameters of the rock through which the borehole passes. In a test in which the rock was simulated by solid aluminum for calibration purposes, a cone having an apex angle $\alpha$ of 62 degrees was used which provided an angle of incidence of 28 degrees, which is the critical angle for shear waves but is well beyond the critical angle for compressional waves. Even in this case the compressional waves were detected by the receiving transducer. This is believed to be due to imperfections in the transmitting transducer 6 and the cone 8. One of these imperfections is the edge effect of element 6 mentioned above and these results indicate that elimination of the transducer edge effects would not be beneficial. The reflector 8 would also tend to cause refraction of energy which impinges upon it at its lower edge. The reflecting surface of reflector 8 may also not be a perfect reflector and cause some diffusion and thereby spread the raypaths.

Figure 2A:
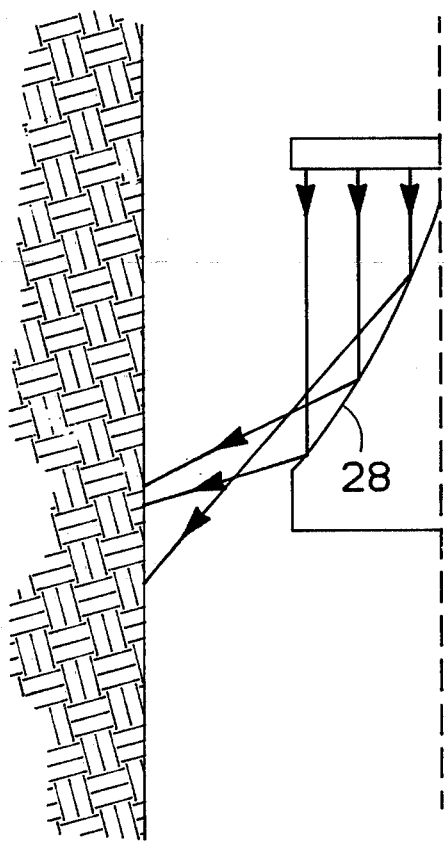
FIG. 2 is a cross-sectional illustration of two modified forms of transducer assemblies according to the present invention.
Figure 2B:
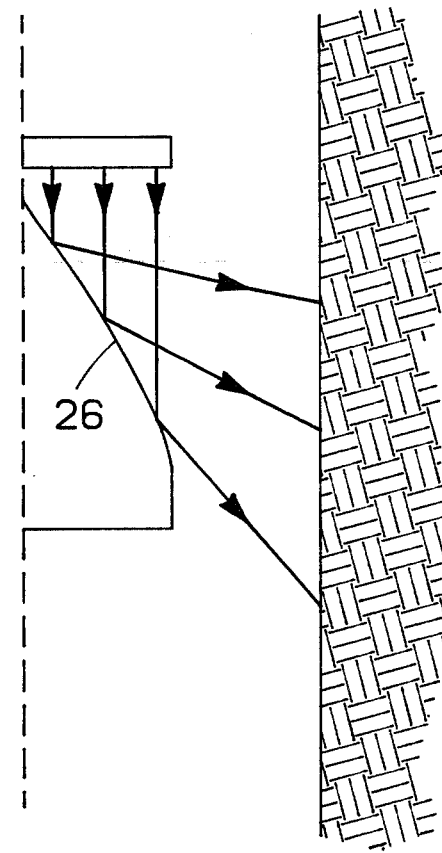

A modification of cone 8 to intentionally spread the reflected energy over a narrow band of angles is believed to be advisable for actual borehole work. FIGS. 2(a) and 2(b) show the right and left halves of cones having convex and concave reflecting surfaces 26, 28, respectively. The amounts of curvature are greatly exaggerated for purposes of illustration. The convex surface 26 causes a spreading of the raypaths at the borehole wall, while the concave survace 28 has a focusing effect which may be beneficial. In either case the curvature causes energy to impinge on the wall over a controllable and selectable range of angles. As illustrated, the curvature is not linear and the rate of curvature increases with distance from the axis of the cone. This variation is to cause equal amounts of energy to be transmitted in each of the angular increments.

Curving the cone surface would make it easier to get equal increments of energy into the pressure and shear waves induced into the borehole wall. This effect would be somewhat similar to that taught in the above-referenced Trouiller patent, but has one great advantage. The Trouiller device insures that some energy will impinge upon the borehole wall at the critical angle by using an omnidirectional transducer which sends out equal amounts of energy in all directions radial to the transducer element axis. Thus, if energy impinging upon the wall over a 20-degree spread of angles is effectively coupled and transmitted to the receiving transducers, only 1/18 of the energy transmitted by the transducers taught by Trouiller is effectively utilized. In contrast, substantially all of the energy transmitted from the transducer 6 of the present invention is deflected by cone 8 into a cone-shaped energy spread which can be directed at the borehole wall within a narrow range of incidence angles. Thus, if a 20-degree spread of angles is desired at the borehole wall, the cone 8 may have a curved surface wherein the angle with respect to the borehole axis varies by 10 degrees from the point or apex to the skirt of the cone. Such a cone would direct substantially all of the energy from element 6 at the borehole wall within a 20-degree angle of incidence spread.

It is anticipated that the transducer assemblies of the present invention will be useful in improved borehole compensated logging tools. Such tools typically have two transmitters and four receivers. The transmitters are positioned at the upper and lower ends of the tool and the receivers located near the center. The upper transmitter is used to transmit to two of the receivers and the lower to the other two, but not at the same time. The upward and downward signals are distinguished only by time switching the various transducers. The purpose is to compensate for borehole variations by combining readings taken from waves traveling both directions. With directional transducers as taught herein, upper and lower transmitters can be fired simultaneously and their respective signals can be separated by directional receivers. In this way errors, such as change of tool position between readings, can be reduced.

While the present invention has been illustrated and described with respect to particular apparatus, it is apparent that various modifications to this apparatus may be made within the scope of the present invention as defined by the appended claims.

I claim:

1. A multi-directional electroacoustic transmitting and receiving assembly comprising an electroacoustical transducer element having a planar acoustical energy transmitting surface and an essentially symmetrical conical reflector positioned substantially centrally in the path of acoustical energy transmitted from said planar surface, with the axis of said symmetrical conical reflector being essentially perpendicular to said planar surface and substantially parallel to the direction of propagation of said acoustical energy from said planar surface, wherein the angle of said conical reflector surface relative to its axis varies from the apex to the skirt of said reflector, thereby forming a curved surface whereby the reflected energy is reflected over a range of directions, all of said directions being away from the plane of said acoustic energy transmitting surface.

2. An assembly according to claim 1 wherein said transducer element is a magnetostrictive device.

3. An assembly according to claim 1 wherein said transducer element is a piezoelectric device.

4. An assembly according to claim 1 wherein the apex angle of said conical reflector is selected to direct energy from said transducer element at angles relative to the substantially conical reflector axis near one or more expected critical angles for a borehole wall into which said energy is to be transmitted or from which said energy is to be received.

5. In a sonic borehole logging device of the type having one or more electroacoustic transmitting assemblies for transmitting acoustic energy into a borehole wall at a first point and one or more electroacoustic receiving assemblies for receiving acoustic energy from said borehole wall at one or more points spaced vertically from said first point, an improved transmitter assembly comprising an electroacoustical transducer element having a planar acoustical energy transmitting surface and an essentially symmetrical conical reflector positioned substantially centrally in the path of acoustical energy transmitted from said planar surface with the axis of said symmetrical conical reflector being essentially perpendicular to said planar surface and substantially parallel to the direction of propagation of said acoustical energy from said planar surface, wherein the angle of said conical reflector surface relative to its axis varies from the apex to the skirt of said reflector, thereby forming a curved surface whereby the reflected energy is reflected over a range of directions, all of said directions being away from the plane of said energy transmitting surface, and an improved receiving assembly, substantially equivalent to said transmitting assembly, further being capable of receiving said transmitted acoustic energy from said improved transmitting assembly, said improved receiving assembly being positioned substantially centrally along the same axis as said transmitter assembly and remote therefrom, said receiving assembly being inverted end for end with respect to said transmitter assembly configuration within said logging device.

6. A device according to claim 5 wherein said transducer element is a magnetostrictive device.

7. A device according to claim 5 wherein said transducer element is a piezoelectric device.

8. A method for transmitting multi-directional acoustic energy comprising the steps of:

generating acoustical energy with an electroacoustical transducer element having a planar acoustical energy transmitting surface, and reflecting said acoustical energy with an essentially symmetrical conical reflector positioned substantially centrally in the path of said acoustic energy, the axis of said symmetrical conical reflector being essentially perpendicular to said planar surface and substantially parallel to the direction of propagation of said acoustical energy from said planar surface, wherein the angle of said conical reflector surface relative to its axis varies from the apex to the skirt of said reflector, thereby forming a curved surface whereby the reflected energy is reflected over a range of directions, all of said directions being away from the plane of said acoustic energy transmitting surface.

9. The method of claim 8 wherein said transducer element is a magnetostrictive device.

10. The method of claim 8 wherein said transducer element is a piezoelectric device.

11. The method of claim 8 wherein the apex angle of said conical reflector is selected to direct energy from said transducer element at angles relative to the substantially conical reflector axis near one or more expected critical angles for a borehole wall into which said energy is to be transmitted.

12. A method for sonic borehole logging wherein one or more electroacoustic transmitting assemblies are used to transmit acoustic energy into a borehole wall at a first point and one or more electroacoustic receiving assemblies are used to receive acoustic energy from said borehole wall at one or more points spaced vertically from said first point, said method comprising the steps of:

generating said acoustic energy with an improved transmitter assembly comprising an electroacoustical transducer element having a planar acoustical transmitting surface and an essentially symmetrical conical reflector positioned substantially centrally in the path of acoustical energy transmitted from said planar surface with the axis of said symmetrical conical reflector being essentially perpendicular to said planar surface and substantially parallel to the direction of propagation of said acoustical energy from said planar surface, wherein the angle of said conical reflector surface relative to its axis varies from the apex to the skirt of said reflector, thereby forming a curved surface whereby the reflected energy is reflected over a range of directions, all said directions being away from the plane of said energy transmitting surface, and receiving said acoustical energy with an improved receiving assembly, substantially equivalent to said transmitting assembly, said improved receiving assembly being positioned substantially centrally along the same axis as said transmitter assembly and remote therefrom, said receiving assembly being inverted end-for-end with respect to said transmitter assembly configuration.

13. The method of claim 12 wherein said transducer element is a magnetostrictive device.

14. The method of claim 12 wherein said transducer element is a piezoelectric device.

* * * * *